US010321838B2

(12) United States Patent
Herleikson

(10) Patent No.: US 10,321,838 B2
(45) Date of Patent: Jun. 18, 2019

(54) ACTIVE LOW IMPEDANCE ELECTRODE

(71) Applicant: KONINKLIJKE PHILIPS N.V., Eindhoven (NL)

(72) Inventor: Earl Clark Herleikson, Cinebar, WA (US)

(73) Assignee: Koninklijke Philips N.V., Eindhoven (NL)

( * ) Notice: Subject to any disclaimer, the term of this patent is extended or adjusted under 35 U.S.C. 154(b) by 374 days.

(21) Appl. No.: 15/110,203

(22) PCT Filed: Jan. 7, 2015

(86) PCT No.: PCT/IB2015/050112
§ 371 (c)(1),
(2) Date: Jul. 7, 2016

(87) PCT Pub. No.: WO2015/104657
PCT Pub. Date: Jul. 16, 2015

(65) Prior Publication Data
US 2016/0331256 A1    Nov. 17, 2016

Related U.S. Application Data

(60) Provisional application No. 61/924,255, filed on Jan. 7, 2014.

(51) Int. Cl.
*A61B 5/0428*     (2006.01)
*A61B 5/0408*     (2006.01)
(Continued)

(52) U.S. Cl.
CPC ........ *A61B 5/0408* (2013.01); *A61B 5/04004* (2013.01); *A61B 5/0428* (2013.01); *A61B 5/0478* (2013.01); *A61B 5/7203* (2013.01)

(58) Field of Classification Search
CPC ... A61B 5/024; A61B 5/02444; A61B 5/0255; A61B 5/04; A61B 5/04004;
(Continued)

(56) References Cited

U.S. PATENT DOCUMENTS 3,880,146 A    4/1975 Everett et al.
8,454,505 B2   6/2013 Yazicioglu et al.
(Continued)

FOREIGN PATENT DOCUMENTS

CN    103197109 A    7/2013
CN    104079164 A    10/2014

OTHER PUBLICATIONS

Metting Van Rijn, A. et al., "Low-cost Active Electrode Improves the Resolution in Biopotential Recordings", 18th Annual International Conference of the IEEE Engineering in Medicine and Biology Society, Amsterdam, 1996.
(Continued)

*Primary Examiner* — Eugene T Wu

(57) ABSTRACT

An active low impedance electrode (20) employing an electrical activity sensor (21) connected to a voltage sense contact (22), a current flow contact (23) and an active electrode coupler (24). In operation, responsive to the voltage sense contact (22) and the current flow contact (23) being attached to the anatomical region (13) of the patient, the electrical activity sensor (21) controls a directional flow of a sensor current between the electrical activity sensor (21) and the anatomical region (13) to establish an equivalence between a patient voltage at voltage sense contact (22) and a sensor voltage at active electrode coupler (24), and/or a patient contact impedance between the voltage sense contact (22) and the current flow contact (23) is greater than an active electrode impedance at the active electrode coupler (24).

15 Claims, 3 Drawing Sheets

(51) Int. Cl.
*A61B 5/04* (2006.01)
*A61B 5/0478* (2006.01)
*A61B 5/00* (2006.01)

(58) Field of Classification Search
CPC ... A61B 5/0402; A61B 5/0408; A61B 5/0428; A61B 5/0444; A61B 5/0448; A61B 5/0476; A61B 5/0478; A61B 5/72; A61B 5/7203; A61B 5/7207; A61B 5/721; A61B 5/7214; A61B 5/7225
See application file for complete search history.

(56) References Cited

U.S. PATENT DOCUMENTS

| | | |
|---|---|---|
| 2001/0021813 A1 | 9/2001 | Yonce |
| 2003/0006782 A1 | 1/2003 | Shambroom et al. |
| 2011/0001497 A1 | 1/2011 | Chetelat et al. |
| 2011/0295096 A1 | 12/2011 | Bibian et al. |
| 2012/0095361 A1 | 4/2012 | Xu et al. |
| 2012/0116198 A1* | 5/2012 | Veen .................. A61B 5/04284 600/372 |
| 2013/0204154 A1 | 8/2013 | Loi et al. |
| 2015/0109007 A1 | 4/2015 | Townsend |

OTHER PUBLICATIONS

Degen, T., et al., "A Pseudodifferential Amplifier for Bioelectric Events with DC-Offset Compensation Using Two-Wired Amplifying Electrodes", IEEE Transactions on Biomedical Engineering, vol. 53, No. 2, Feb. 2006.

* cited by examiner

ACTIVE LOW IMPEDANCE ELECTRODE

This application is a national stage application under 35 U.S.C. § 371 of International Application No. PCT/IB2015/050112 filed on Jan. 7, 2015 and published in the English language on Jul. 16, 2015 as International Publication No. WO 2015/104657, which claims priority to U.S. Application No. 61/924,255 filed on Jan. 7, 2014, the entire disclosures of which are incorporated herein by reference.

FIELD OF THE INVENTION

The present invention generally relates to electrodes utilized by an electrical activity monitor for recording electrical activity of a biological organ (e.g., an electrocardiogram ("ECG") monitor for recording electrical activity of a patient's heart and an electroencephalogram ("EEG") monitor for recording electrical activity of a patient's brain). The present invention specifically relates to electrodes actively providing a low contact impedance for the ECG/EEG patient.

BACKGROUND OF THE INVENTION

As known in the art, ECG/EEG systems measure the voltages on a skin surface of a patient. These measured voltages are typically less than 1 mV. Of note is a skin electrode interface impedance may vary dramatically from patient to patient. For example, these impedances may vary between 10K ohms and 10M ohms for a typical connection to the patient with standard electrodes. Such high impedances however are problematic with the use of standard electrodes.

More particularly, any electrostatic coupling into a wire that connects the electrode to an amplifier input of a ECG/EEG monitor will result in current flow across the patient impedance, and any artifact signal generated by such an electrostatic coupling is directly proportional to the impedance of the electrode skin interface. To impede the generation of artifact signals, ECG/EEG monitors currently use shielded wires in order to minimize any electrostatic coupling.

In addition to the direct coupling into an individual wire, electrostatic coupling may occur in a common mode coupling to the patient. Specifically, as implemented in the art, ECG/EEG monitors use one electrode as a reference electrode to provide for current flow between the patient and the ECG/EEG monitors. Typically, an active feedback loop is used to force most of the common mode current to flow through the reference electrode and minimize a common mode signal present on the measurement electrodes. The amplitude of the common mode signal is equal to current of the common mode coupling times the reference electrode impedance divided by the loop gain of the active feedback loop. The remaining signal then is cancelled by the matching of the input amplifiers in the input circuitry of the ECG/EEG monitors.

In the case of emergency response where the patient is transported in an ambulance while being closely monitored for ECG, the sources of electrostatic coupling are substantial. For example, many possible sources of statically charged bodies are in the ambulance, and movement of charged bodies when driving down a road is very probable. Consequently, a patient with high contact impedance electrodes will typically have significant artifact present in the ECG when the ambulance is in motion, and the ambulance will have to pull over and stop in order to perform a 12-lead static-free ECG measurement to transmit to the hospital.

Likewise, sources of electrostatic coupling may be substantial for a patient being closely monitored for EEG.

SUMMARY OF THE INVENTION

To address the disadvantages of the prior art, the present invention provides an electrode for actively reducing the skin electrode contact impedance to thereby minimize the effects of any electrostatic coupled signals on the ECG/EEG waveform. This substantially improves the quality of the ECG/EEG measurement, especially in presence of substantial electrostatic sources (e.g., a case of patient transport). With low electrode source impedance, a shielding of ECG/EEG cabling is not necessary, and an elimination of the shielding for the ECG/EEG cables consequently allows for low cost disposable ECG/EEG cables.

One form of the present invention is an active low impedance electrode employing an electrical activity sensor connected to a voltage sense contact, a current flow contact and an active electrode coupler. In operation, responsive to the voltage sense contact and the current flow contact being attached to the anatomical region of the patient, the electrical activity sensor controls a directional flow of a sensor current between the electrical activity sensor and the anatomical region to establish an equivalence between a patient voltage at voltage sense contact and a sensor voltage at active electrode coupler, and/or a patient contact impedance between the voltage sense contact and the current flow contact is greater than an active electrode impedance at the active electrode coupler.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

To facilitate understanding of the present invention, exemplary embodiments of the present invention will be provided herein directed to an electrical activity monitoring of a biological organ of a patient via an active low impedance electrode connecting an anatomical region of the patient to the electrical activity monitor.

Figure 1:
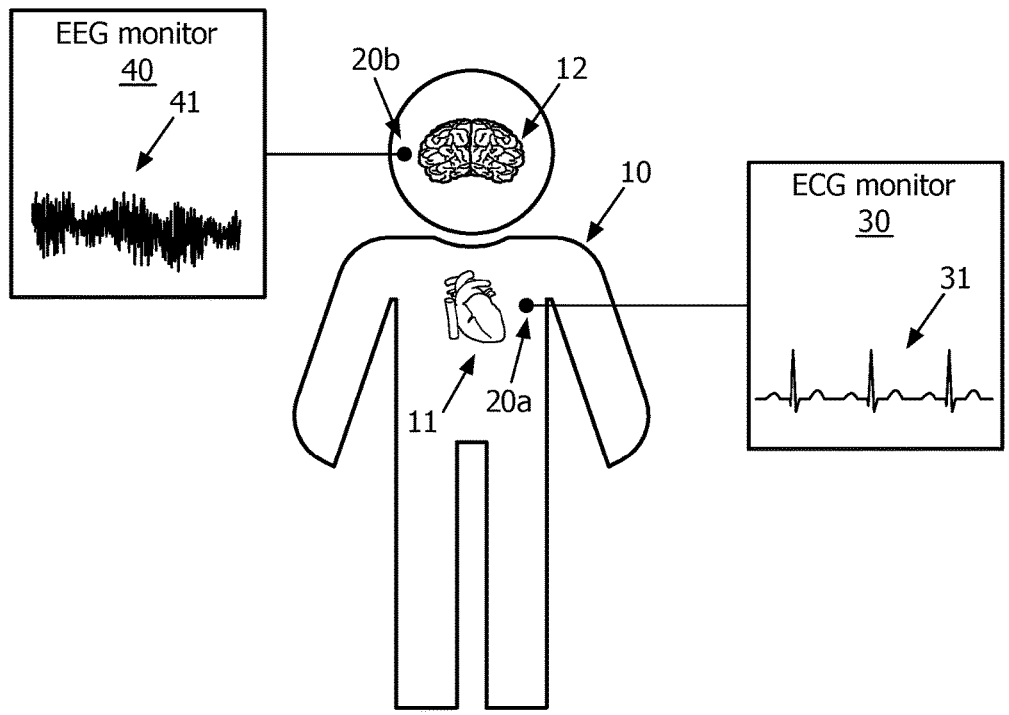
FIG. 1 illustrates exemplary embodiments of an electrical monitoring system in accordance with the present invention.

For example, FIG. 1 illustrates a known ECG monitor 30 recording electrical activity 31 of a heart 11 of a patient 10 via an active low impedance electrode 20a of the present invention connecting a thoracic region of patient 10 to ECG monitor 30. Also by example, FIG. 1 illustrates known EEG monitor 40 recording electrical activity 41 of a brain 12 of a patient 10 via an active low impedance electrode 20b of the present invention connecting a cranial region of patient 10 to EEG monitor 40.

While only one electrode 20a is shown for ECG monitor 30 and only one electrode 20b is shown for EEG monitor for clarity of FIG. 1, one or more active low impedance electrodes 20 of the present invention are employed in practice for a recording of electrical activity within an anatomical region as would be appreciated by one skilled in the art, and one or more conventional electrodes may be additionally employed in practice for the recording of electrical activity within the anatomical region as would be appreciated by one skilled in the art.

Figure 2:
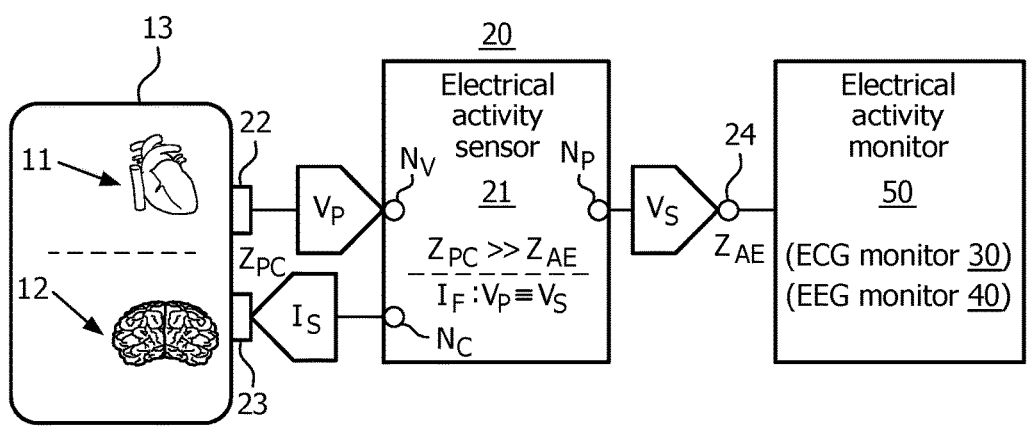
FIG. 2 illustrates an exemplary embodiment of an active low impedance electrode in accordance with the present invention.

Referring to FIG. 2, an active low impedance electrode 20 of the present invention employs an electrical activity sensor 21, a voltage sense contact 22, a current flow contact 23 and an active electrode coupler 24. In practice, voltage sense contact 22 and current flow contact 23 are attached as known in the art to an anatomical region 13 of patient 10 (e.g., the cranial region or the thoracic region of FIG. 1), and active electrode coupler 24 is connected as known in the art to an electrical activity monitor 50 (e.g., ECG monitor 30 or EEG monitor 40 of FIG. 1).

Voltage sense contact 22 applies a patient voltage $V_P$ on a skin surface of anatomical region 13 to a voltage node $N_V$ of electrical activity sensor 21 having a high input impedance that effectively impedes any current flow from anatomical region 13 into voltage sense contact 22. As known in the art, fluctuation(s) of patient voltage $V_P$ are indicative of electrical activity of a biological organ within anatomical region 13 (e.g., heart 11 or brain 12 of FIG. 1).

Current flow contact 23 controls a directional flow of a sensor current $I_S$ between electrical anatomical region 13 and a current node $N_C$ of electrical activity sensor 21 having a low source impedance that effectively directs any current flow from anatomical region 13 through current flow contact 23. The aforementioned attachment of voltage sense contact 22 and current flow contact 23 to anatomical region 13 flow sensor current $I_S$ equaling a voltage drop between voltage sense contact 22 and current flow contact 23 divided by a patient contact impedance $Z_{PC}$. This facilitates a sensing of patient voltage $V_P$ by electrical activity sensor 21, particularly in a presence of a substantial flow of sensor current $I_S$ into anatomical region 13.

Active electrode coupler 24 applies a sensor voltage $V_S$ at a power node $N_P$ of electrical activity sensor 21 to electrical activity monitor 50. Sensor voltage $V_S$ is representative of patient voltage $V_P$ whereby electrical activity monitor 50 may measure and record the electrical activity of the biological organ within anatomical region 13. Of importance is an impedance $Z_{AE}$ of active electrode coupler 24 is significantly less (>>) than patient contact impedance $Z_{PC}$.

In operation, electrical activity sensor 21 generates sensor voltage $V_S$ and controls a directional flow of sensor current $I_S$ to establish an equivalence (≡) of patient voltage $V_P$ to sensor voltage $V_S$ whereby any fluctuation of sensor voltage $V_S$ mirrors any fluctuation of voltage patient voltage $V_P$.

Figure 3:
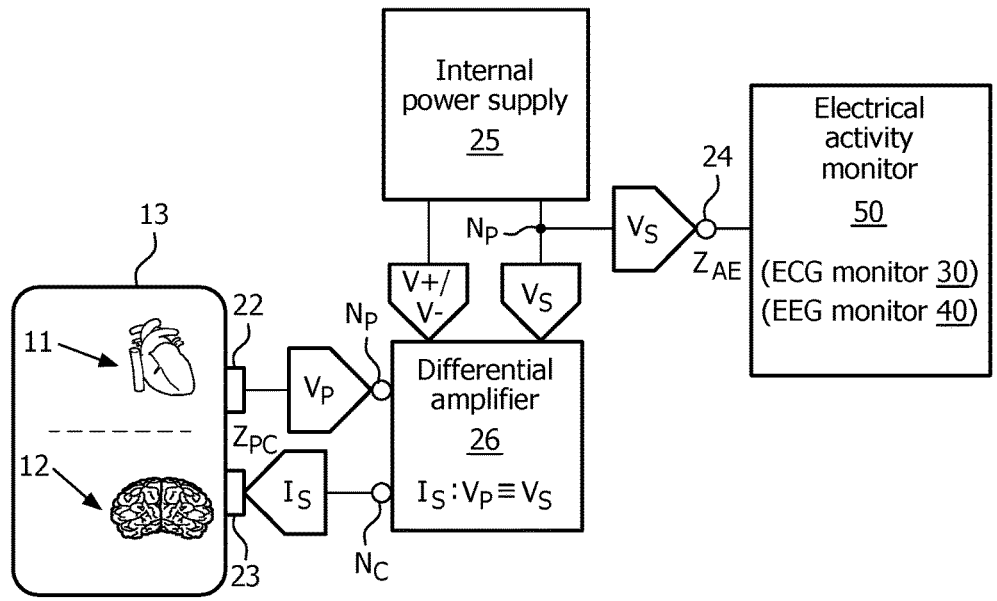
FIG. 3 illustrates an exemplary embodiment of an electrical activity sensor of the present invention as shown in FIG. 2.
Figure 4:
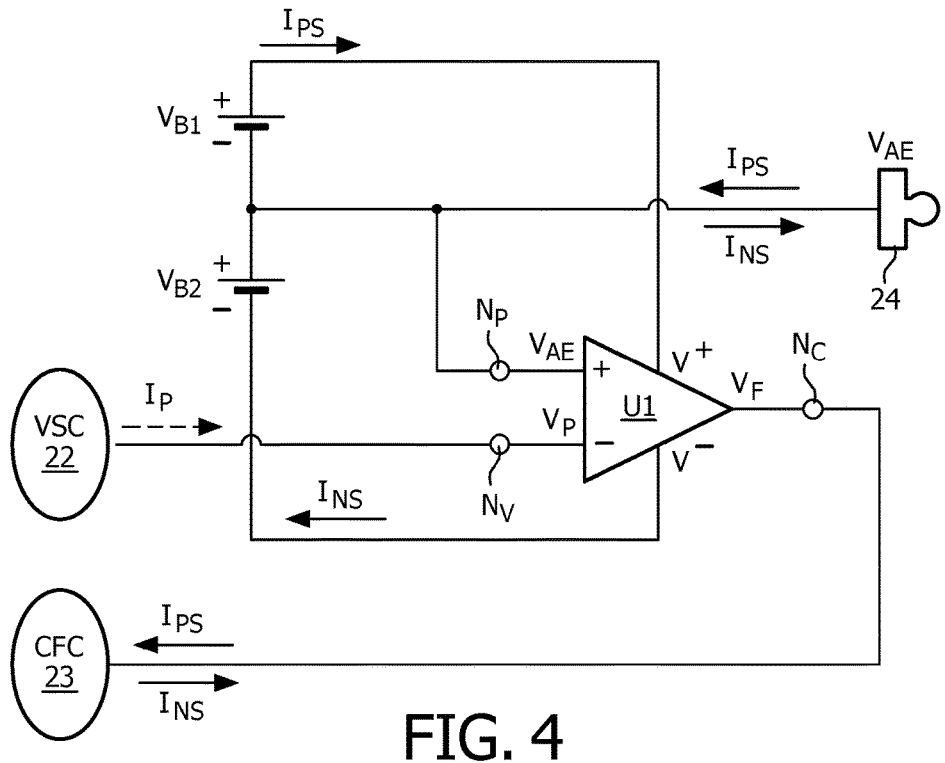
FIG. 4 illustrates an exemplary schematic embodiment of the electrical activity sensor shown in FIG. 2.

A block diagram of an exemplary embodiment of electrical activity sensor 21 is shown in block diagram shown in FIG. 3 and a schematic diagram of an exemplary embodiment of electrical activity sensor 21 is shown in FIG. 4.

Referring to FIGS. 3 and 4, the exemplary embodiment of electrical activity sensor 21 employs an internal power supply 25 and a differential amplifier 26 as shown in FIG. 3. Internal power supply 25 in the form of a split power supply as shown in FIG. 4 includes a series connection of two (2) small battery cells $V_{B1}$ and $V_{B2}$ for powering differential amplifier 26 in the form of a low power operational amplifier ("op-amp") U1 via a connection to power/negative power supplies V+/V− of op-amp U1 as shown in FIG. 4. A center point of the series connection of battery cells $V_{B1}$ and $V_{B2}$, a non-inverting input (+) of op-amp U1 and active electrode coupler 24 are connected to power node $N_P$. voltage sense contact ("VSC") 22 and an inverting input (−) of op-amp U1 and are connected to voltage node $N_V$. Inverting input (−) of operational amplifier U1 has a high input impedance that effectively impedes any flow of current $I_P$ from anatomical region 13 (FIG. 2) through voltage sense contact 22 to op-amp U1.

Current flow contact ("CFC") 23 and an output of op-amp U1 are connected to current node $N_C$ whereby a feedback path of op-amp U1 from output to inverting input (−) includes voltage sense contact 22 and current low contact 23. Specifically, in response to anatomical region 13 being connected to voltage sense contact 22 and current flow contact 23, a feedback of op-amp U1 will drive patient voltage $V_P$ to sensor voltage $V_S$ at non-inverting input (+) of operational amplifier U1 generated by the center point of the series connection of battery cells $V_{B1}$ and $V_{B2}$. Therefore, sensor voltage $V_S$ at active electrode coupler 24 becomes approximately equivalent to patient voltage $V_P$ at voltage sense contact 22. The larger a loop gain of op-amp U1, then the closer sensor voltage $V_S$ at active electrode coupler 24 will match patient voltage $V_P$ at voltage sense contact 22.

Sensor current $I_S$ as shown in FIG. 3 may have a positive current flow $I_{PS}$ as shown in FIG. 4 from battery cell $V_{B1}$ to positive power supply (V+) of operational amplifier U1 through an output drive circuitry of operational amplifier U1 to anatomical region 13 via current flow contact 23. Conversely, sensor current $I_S$ as shown in FIG. 3 may have a negative current flow $I_{NS}$ as shown in FIG. 4 from anatomical region 13 via current flow contact 23 through output drive circuitry of op-amp U1 to battery cell $V_{B2}$ via negative power supply (V−) of op-amp U1. A voltage drop between voltage sense contact 22 and current flow contact 23 is a function of sensor current $I_S$ times a contact impedance of current flow contact 23. The equivalent contact impedance of the electrode is the voltage difference between $V_{AE}$ and $V_P$ divided by sensor current $I_S$ flowing through active electrode coupler 24. The difference between $V_{AE}$ and $V_P$ is equal to $V_F$ divided by the open loop gain of op-amp U1. Therefore, an equivalent contact impedance of this active electrode 20 is the contact impedance of current flow contact 23 divided by the open loop gain of op-amp U1.

In practice, active low impedance electrode 20 as shown in FIG. 4 demonstrated a reduction in the electrode impedance. For example, at 5 Hz, which is the center of a ECG bandwidth, the active electrode impedance was only 430 ohms. The impedance of the contact with the patient at this frequency is 10M ohms. Also by example, at 60 Hz, active low impedance electrode 20 reduced the electrode impedance from 8M ohms down to 4.1K ohms. This performance was achieved with a low power op-amp U1 operating with only 1 uA of power supply current from internal power supply 25.

Figure 5A:
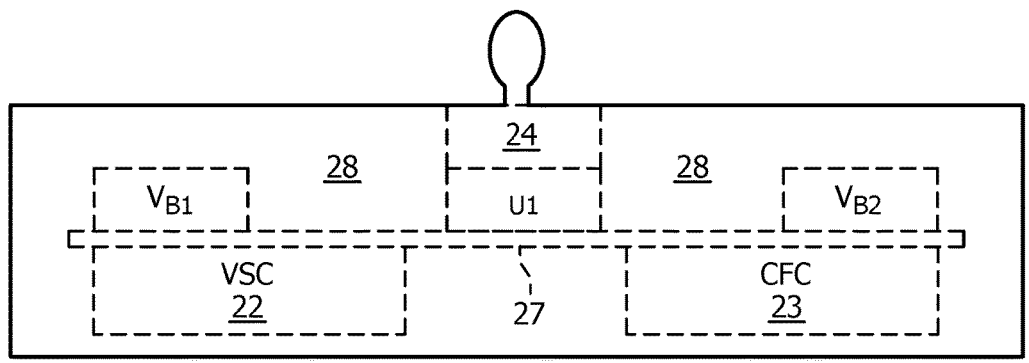
FIGS. 5A-5C respectively illustrate side, top and bottom views, of an exemplary assembly of an active low impedance electrode shown in FIG. 4.
Figure 5B:
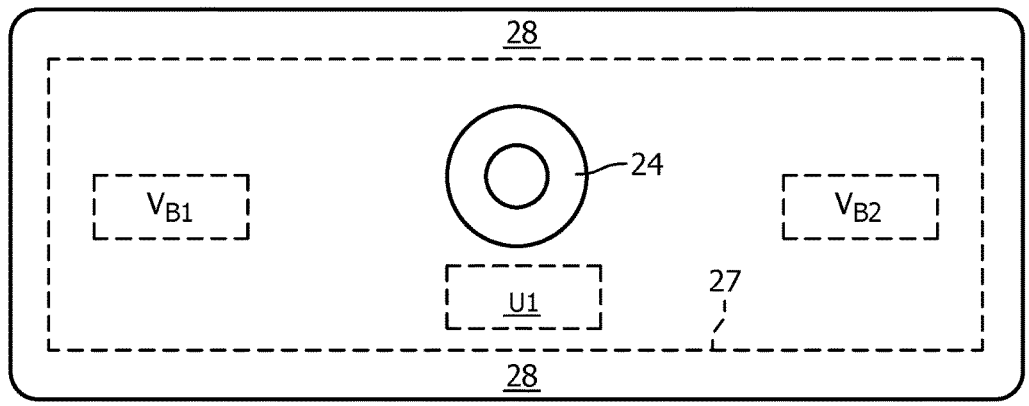
Figure 5C:
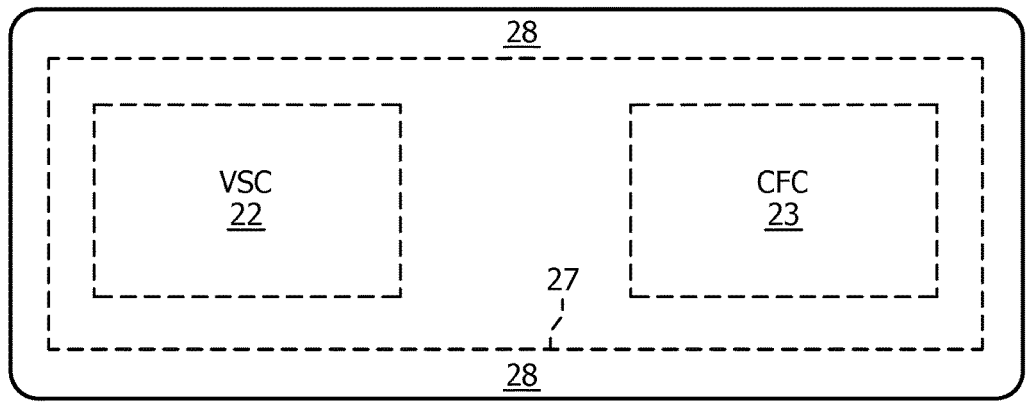

FIGS. 5A-5C illustrate an exemplary assembly of active low impedance electrode 20 as shown in FIG. 4. Specifically, a flexible printed circuit board 27 mechanically supports and electrical connects battery cells $V_{B1}$ and $V_{B2}$, op-amp U1, voltage sense contact 22, current flow contact 23 and active electrode coupler 24 within a foam adhesive 28.

In practice, battery cells $V_{B1}$ and $V_{B2}$ preferably become activated upon active low impedance electrode 20 being removed from the packaging. A zinc air battery cells would be a good solution for this application. Alternatively, other mechanisms may be implemented to actively connect battery cells $V_{B1}$ and $V_{B2}$ to op-amp U1 when voltage sense contact 22, current flow contact 23 are applied to a patient. For example, a force of snapping the electrode wire on to active low impedance electrode 20 could activate battery cells $V_{B1}$ and $V_{B2}$.

Also in practice, op-amp U1 is commercially available with a power supply current less than 10 uA, which would allow active low impedance electrode 20 to operate for a full length of time that it is applied to the patient even with very small battery cells $V_{B1}$ and $V_{B2}$. Op-amp U1 reduces the electrode impedance by the amount of gain. For example active low impedance electrode 20 with a 150 KHz gain bandwidth will have a gain of 1000 at 150 Hz which is the high end of the ECG spectrum. A patient skin electrode impedance of 1 Mohm will look like an impedance of only 1 Kohm at the ECG/EEG connection to ECG/EE monitoring device with an amplifier gain of 1000.

Referring to FIGS. 1-5, those having ordinary skill in the art will appreciate numerous benefits of the present invention including, but not limited to, a backward compatibility with standard electrode systems whereby an improvement of low contact impedance with a patient may be achieved without requiring any change in the known device or cabling hardware.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An active low impedance electrode, comprising:
    an electrical activity sensor including a voltage node, a current node and a power node;
    a voltage sense contact connected to the voltage node and attachable to an anatomical region of a patient to apply a patient voltage to the electrical activity sensor when the voltage sense contact is attached to the anatomical region of a patient, the patient voltage being indicative of an electrical activity of the anatomical region of the patient;
    a current flow contact connected to the current node and attachable to the anatomical region of the patient to facilitate a directional flow of sensor current between the electrical activity sensor and the anatomical region of the patient when the current flow contact is attached to the anatomical region of the patient;
    an active electrode coupler connected to the power node; and
    wherein, responsive to the voltage sense contact and the current flow contact being attached to the anatomical region of the patient, the electrical activity sensor is configured to control the directional flow of the sensor current between the electrical activity sensor and the anatomical region to establish an equivalence between the patient voltage at voltage sense contact and a sensor voltage at active electrode coupler.

2. The active low impedance electrode of claim 1, wherein the electrical activity sensor includes:
    a differential amplifier connected to the voltage node, the current node and the power node.

3. The active low impedance electrode of claim 2, wherein the differential amplifier includes:
    an operational amplifier (U1) having a non-inverting input connected to the power node, an inverting input connected to the voltage node and an output connected to the current node.

4. The active low impedance electrode of claim 1, wherein the electrical activity sensor includes:
    an internal power supply connected to the power node.

5. The active low impedance electrode of claim 4, wherein the internal power supply includes:
    a split power supply ($V_{B1}$, $V_{B2}$) connected to the power node.

6. The active low impedance electrode of claim 4, wherein the electrical activity sensor includes:
    a differential amplifier connected to the internal power supply.

7. The active low impedance electrode of claim 6,
    wherein the internal power supply includes a split power supply ($V_{B1}$-$V_{B2}$); and
    wherein the differential amplifier includes an operational amplifier (UI) having power supplies connected to the split power supply ($V_{B1}$, $V_{B2}$).

8. An active low impedance electrode, comprising:
    an electrical activity sensor including a voltage node, a current node and a power node;
    a voltage sense contact connected to the voltage node and attachable to the an anatomical region of a patient to apply a patient voltage to the electrical activity sensor when the voltage sense contact is attached to the anatomical region of the patient, the patient voltage being indicative of an electrical activity of the anatomical region of the patient;
    a current flow contact connected to the current node and attachable to the anatomical region of the patient to facilitate a directional flow of sensor current between the electrical activity sensor and the anatomical region of the patient when the current flow contact is attached to the anatomical region of the patient;
    an active electrode coupler connected to the power node; and
    wherein, responsive to the voltage sense contact and the current flow contact being attached to the anatomical region of the patient, a patient contact impedance between the voltage sense contact and the current flow contact is greater than an active electrode impedance at the active electrode coupler.

9. The active low impedance electrode of claim 8, wherein the electrical activity sensor includes:
    a differential amplifier connected to the voltage node, the current node and the power node.

10. The active low impedance electrode of claim 9, wherein the differential amplifier includes:

an operational amplifier (U1) having a non-inverting input connected to the power node, an inverting input connected to the voltage node and an output connected to the current node.

11. The active low impedance electrode of claim 8, wherein the electrical activity sensor includes:
an internal power supply connected to the power node.

12. The active low impedance electrode of claim 11, wherein the internal power supply includes:
a split power supply ($V_{B1}$, $V_{B2}$) connected to the power node.

13. The active low impedance electrode of claim 11, wherein the electrical activity sensor includes:
a differential amplifier connected to the internal power supply.

14. The active low impedance electrode of claim 13,
wherein the internal power supply includes a split power supply ($V_{B1}$, $V_{B2}$); and
wherein the differential amplifier includes an operational amplifier (UI) having power supplies connected to the split power supply ($V_{B1}$, $V_{B2}$).

15. An active low impedance electrode, comprising:
an electrical activity sensor including a voltage node, a current node and a power node;
a voltage sense contact connected to the voltage node and attachable to an anatomical region of the patient to apply a patient voltage to the electrical activity sensor when the voltage sense contact is attached to the anatomical region of the patient, the patient voltage being indicative of an electrical activity of the anatomical region of the patient;
a current flow contact connected to the current node and attachable to the anatomical region of the patient to facilitate a directional flow of sensor current between the electrical activity sensor and the anatomical region when the current flow contract is attached to the anatomical region of the patient;
an active electrode coupler connected to the power node;
wherein, responsive to the voltage sense contact and the current flow contact being attached to the anatomical region of the patient, the electrical activity sensor is configured to control the directional flow of the sensor current between the electrical activity sensor and the anatomical region to establish an equivalence between the patient voltage at voltage sense contact and a sensor voltage at active electrode coupler; and
wherein, further responsive to the voltage sense contact and the current flow contact being attached to the anatomical region of the patient, a patient contact impedance between the voltage sense contact and the current flow contact is greater than an active electrode impedance at the active electrode coupler.

* * * * *